(12) United States Patent
Coates

(10) Patent No.: US 12,096,978 B2
(45) Date of Patent: Sep. 24, 2024

(54) CONTROLLED IRRIGATION FOR NEUROMODULATION SYSTEMS AND ASSOCIATED METHODS

(71) Applicant: Medtronic Ireland Manufacturing Unlimited Company, Dublin (IE)

(72) Inventor: Paul Coates, Corte Madera, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 18 days.

(21) Appl. No.: 17/931,379

(22) Filed: Sep. 12, 2022

(65) Prior Publication Data
US 2023/0000549 A1 Jan. 5, 2023

Related U.S. Application Data

(63) Continuation of application No. 15/959,043, filed on Apr. 20, 2018, now Pat. No. 11,478,298.
(Continued)

(51) Int. Cl.
*A61B 18/14* (2006.01)
*A61B 18/02* (2006.01)
(Continued)

(52) U.S. Cl.
CPC .......... *A61B 18/1492* (2013.01); *A61B 18/02* (2013.01); *A61B 18/1206* (2013.01);
(Continued)

(58) Field of Classification Search
CPC ..... A61B 18/02; A61B 18/06; A61B 18/1206; A61B 18/1492; A61B 2018/00023;
(Continued)

(56) References Cited

U.S. PATENT DOCUMENTS

| | | |
|---|---|---|
| 11,395,694 B2 | 7/2022 | Hata et al. |
| 2002/0123749 A1 | 9/2002 | Jain |

(Continued)

FOREIGN PATENT DOCUMENTS

| | | |
|---|---|---|
| CN | 105120785 A | 12/2015 |
| JP | 2012525933 A | 10/2012 |

OTHER PUBLICATIONS

Kiuchi, et al., "Combined renal and common hepatic artery denervation as a novel approach to reduce cardiometabolic risk: technical approach, feasibility and safety in a pre-clinical model," Clinical Research in Cardiology (2021) 110:740-753, Feb. 26, 2021.

*Primary Examiner* — Tigist S Demie
(74) *Attorney, Agent, or Firm* — Shumaker & Sieffert, P.A

(57) ABSTRACT

Neuromodulation catheter systems with controlled irrigation capabilities and methods for using such systems are disclosed herein. One such method includes, for example, positioning an irrigated neuromodulation catheter at a treatment site within a renal blood vessel of a human patient, delivering neuromodulation energy at the treatment site, and delivering irrigation fluid to the treatment site having characteristics coordinated with the delivered energy. The characteristics can be adjusted to maintain an energy delivery element and/or tissue of the blood vessel at a constant temperature as power is increased. The method can further include monitoring at least one parameter of the tissue and/or of the energy delivery element, and adjusting the neuromodulation energy and/or the characteristics of the irrigation fluid if the at least one parameter falls outside of a treatment range of values.

20 Claims, 11 Drawing Sheets

Related U.S. Application Data

(60) Provisional application No. 62/621,359, filed on Jan. 24, 2018.

(51) Int. Cl.
*A61B 18/12* (2006.01)
*A61F 7/12* (2006.01)
*A61N 1/05* (2006.01)
*A61N 1/36* (2006.01)
*A61N 1/40* (2006.01)
*A61N 7/02* (2006.01)
*A61B 18/00* (2006.01)
*A61B 18/06* (2006.01)
*A61N 7/00* (2006.01)

(52) U.S. Cl.
CPC .............. *A61F 7/12* (2013.01); *A61N 1/0551* (2013.01); *A61N 1/36017* (2013.01); *A61N 1/36031* (2017.08); *A61N 1/40* (2013.01); *A61N 7/02* (2013.01); *A61N 7/022* (2013.01); *A61B 2018/00023* (2013.01); *A61B 2018/00029* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00702* (2013.01); *A61B 2018/00714* (2013.01); *A61B 2018/00744* (2013.01); *A61B 2018/00779* (2013.01); *A61B 2018/00791* (2013.01); *A61B 2018/00875* (2013.01); *A61B 2018/00982* (2013.01); *A61B 2018/0212* (2013.01); *A61B 18/06* (2013.01); *A61B 2018/1407* (2013.01); *A61B 2018/1435* (2013.01); *A61B 2018/1467* (2013.01); *A61B 2218/002* (2013.01); *A61F 2007/126* (2013.01); *A61N 1/0558* (2013.01); *A61N 2007/003* (2013.01)

(58) Field of Classification Search
CPC ........... A61B 2018/00029; A61B 2018/00404; A61B 2018/00434; A61B 2018/00511; A61B 2018/00577; A61B 2018/00642; A61B 2018/00702; A61B 2018/00714; A61B 2018/00744; A61B 2018/00779; A61B 2018/00791; A61B 2018/00875; A61B 2018/00982; A61B 2018/0212; A61B 2018/1407; A61B 2018/1435; A61B 2018/1467; A61B 2218/002
See application file for complete search history.

(56) References Cited

U.S. PATENT DOCUMENTS

| | | | |
|---|---|---|---|
| 2007/0049915 A1* | 3/2007 | Haemmerich | A61B 18/1492 606/41 |
| 2012/0165812 A1 | 6/2012 | Christian | |
| 2012/0245577 A1* | 9/2012 | Mihalik | A61B 18/1492 606/33 |
| 2014/0275993 A1 | 9/2014 | Ballakur | |
| 2016/0095535 A1 | 4/2016 | Hettrick et al. | |

* cited by examiner

CONTROLLED IRRIGATION FOR NEUROMODULATION SYSTEMS AND ASSOCIATED METHODS

CROSS-REFERENCE TO RELATED APPLICATION(S)

The present application is a continuation of U.S. patent application Ser. No. 15/959,043, filed Apr. 20, 2018, which claims the benefit of U.S. Provisional Patent Application No. 62/621,359, filed Jan. 24, 2018; the entire content of each application is incorporated herein by reference in its entirety.

TECHNICAL FIELD

The present technology is related to irrigated neuromodulation systems and associated methods. In particular, various embodiments of the present technology are related to neuromodulation catheter systems with controlled irrigation capabilities and methods for using such systems.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS, in particular, has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

DETAILED DESCRIPTION

Figure 1:
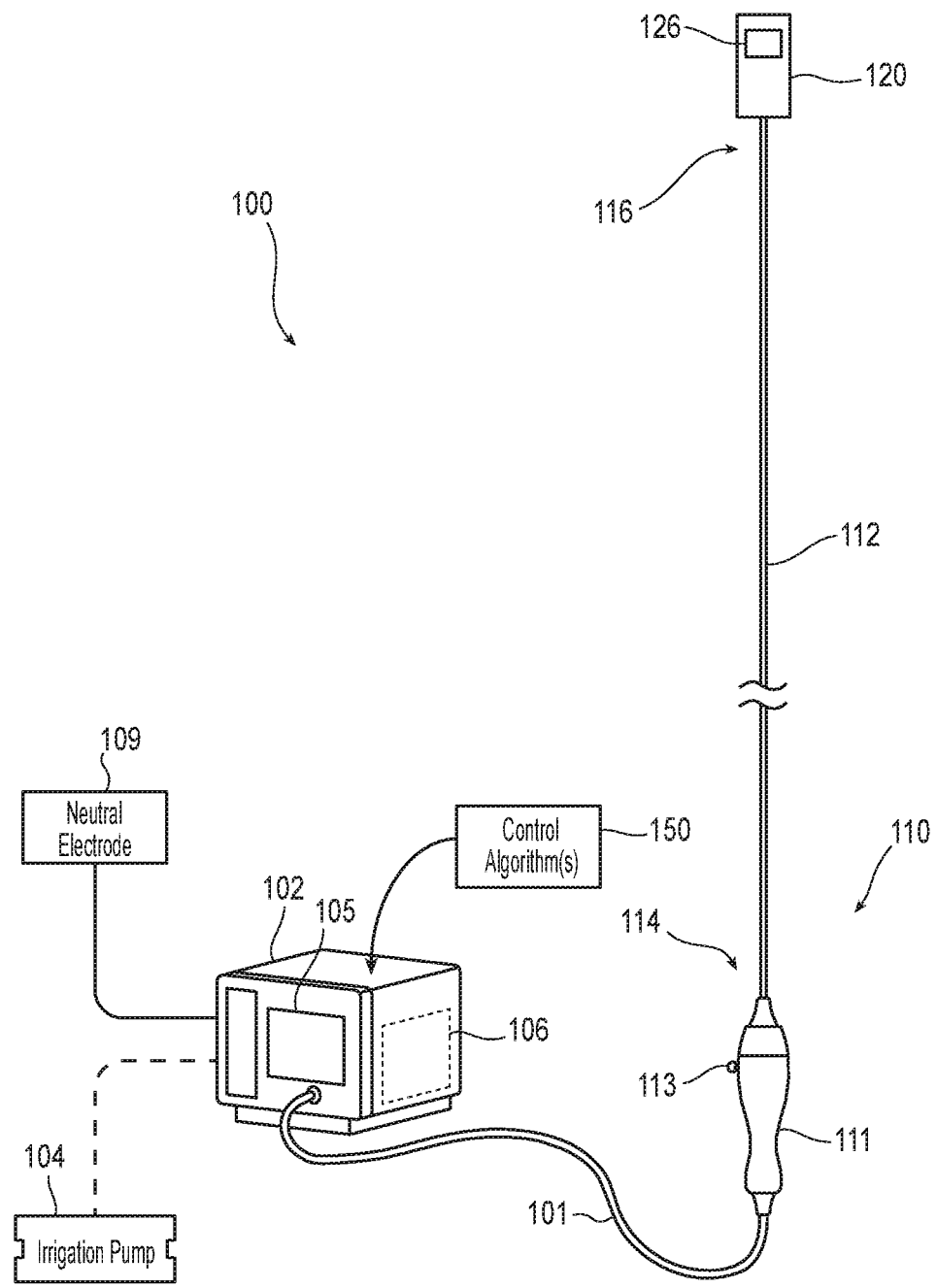
FIG. 1 is a partially schematic perspective view illustrating a renal neuromodulation system including an irrigated treatment device configured in accordance with embodiments of the present technology.

The following disclosure describes neuromodulation catheter systems with controlled irrigation capabilities and methods for using such systems. More specifically, neuromodulation systems configured in accordance with embodiments of the present technology utilize a neuromodulation catheter having an irrigated treatment assembly. The disclosed neuromodulation systems are configured to deliver coordinated neuromodulation energy and irrigation fluid to the irrigated treatment assembly at a treatment site within a blood vessel (e.g., a renal blood vessel) of a patient. The disclosed systems are configured to adjust/modify one or more parameters of energy delivery and irrigation throughout treatment based on, for example, patient tissue characteristics at the treatment site, treatment assembly component characteristics, irrigation fluid characteristics, power at which energy is currently being applied, and other related parameters.

Using conventional neuromodulation systems and methods, a lesion's depth can be increased at a target site within a patient by increasing power at which energy is delivered to the tissue. The temperature of an electrode (or electrodes) used to deliver such energy, however, also increases as power is increased. In some cases, the increased temperature of the electrode can lead to coagulation of blood and charring of the vessel tissue. This tissue damage can, in turn, lead to other adverse effects, including downstream infarction or other undesirable tissue damage. For this reason, some conventional systems incorporate irrigation to provide cooling at the treatment site and to avoid some of the adverse effects experienced with non-irrigated catheters. Nevertheless, irrigated ablation systems have been shown to create undesirably larger lesions than non-irrigated catheters, and several adverse effects associated with tissue damage after use of these irrigated catheters have been documented, including renal artery stenosis, arterial access site issues, and/or significant eGFR decline.

There are several reasons for the continued presence of adverse effects associated with the use of conventional irrigated catheters. For example, irrigation fluid in these conventional systems is typically applied in an uncontrolled fashion, with limited control over flow rates and timing of delivery and limited control over temperature of the infusate. These practices can skew temperature measurements taken by the neuromodulation system during treatment. In particular, irrigation fluid may cause these conventional systems to report an electrode temperature somewhere between the temperature of the irrigation fluid (e.g., room temperature) and a patient's body temperature, which becomes increasingly inaccurate over the course of treatment (especially as power is increased). Thus, in many circumstances, any electrode temperature information conveyed back to the system's generator after use of irrigation fluid cannot reliably be used as a measure of ablation progress. As a result, these conventional irrigated systems inaccurately track the size of the lesions created and the condition of treated tissue. Although this issue not as much of a concern when ablating certain anatomical structures (e.g., heart tissue), this lack of control is especially problematic when ablating near electrically vulnerable, thin-walled, or other arterial structures. For example, renal anatomy is typically more complicated in the local heterogeneity of anatomical structures than heart tissue. Thus, greater control and care when performing renal denervation is required than can be offered by conventional irrigated systems.

In contrast with conventional systems and techniques, neuromodulation systems and methods in accordance with embodiments of the present technology are configured to deliver coordinated neuromodulation energy and irrigation fluid to a treatment site. In some embodiments, these systems and methods are configured to actively monitor characteristics (e.g., temperature, impedance, etc.) of the tissue and/or of the neuromodulation element(s) at the treatment site. The systems and methods can use this diagnostic information to monitor treatment progress and/or to adjust (i) characteristics (e.g., type, power level, duration, frequency, etc.) of neuromodulation energy applied to the treatment site in relation to a control algorithm of the neuromodulation procedure and/or (ii) characteristics (e.g., volume, temperature, type, duration, rate, etc.) of the irrigation fluid delivered to the treatment site. Accordingly, systems configured in accordance with the present technology are expected to achieve greater control of lesion characteristics during the neuromodulation procedure and to improve the likelihood that the neuromodulation procedure will be successful, especially in blood vessels with impaired and/or low blood flow. For example, systems and methods in accordance with embodiments of the present technology are expected to achieve greater lesion depth without the adverse effects noticed in patients after use of conventional systems and methods.

Specific details of several embodiments of the present technology are described herein with reference to FIGS. 1A-13. Although many of the embodiments are described with respect to devices, systems, and methods for intravascular renal neuromodulation, other applications and other embodiments in addition to those described herein are within the scope of the present technology. For example, at least some embodiments of the present technology may be useful for extravascular neuromodulation, intravascular non-renal neuromodulation, and/or use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

A. Selected Embodiments of Neuromodulation Catheters and Systems

FIG. 1 is a partially-schematic diagram illustrating a neuromodulation system 100 configured in accordance with an embodiment of the present technology. The system 100 can include a treatment device 110 (e.g., an irrigated catheter) operably coupled to a console 102 via a connector 101 (e.g., a cable). The system 100 further includes an irrigation pump 104 integrated with the console 102 to facilitate simultaneous and/or coordinated delivery of neuromodulation energy and irrigation fluid during therapy. As shown in FIG. 1, the treatment device 110 can include an elongated shaft 112 having a proximal portion 114, a handle assembly 111 at a proximal region of the proximal portion 114, and a distal portion 116 extending distally relative to the proximal portion 114. The elongated shaft 112 can be configured to locate the distal portion 116 intravascularly (e.g., within a renal artery) or within another suitable body lumen (e.g., within a ureter) at a treatment location. The treatment device 110 can further include a treatment assembly 120 carried by or affixed to the distal portion 116 of the elongated shaft 112. The treatment assembly 120 can include one or more neuromodulation elements 126 (shown schematically in FIG. 1) configured to deliver a therapeutic energy or compound to a nerve located at least proximate to a wall of a body lumen. In some embodiments, the handle 111 can include an actuator 113 to convert the treatment assembly 120 between a delivery state and a deployed state via a guide wire (not shown) and remote actuation of the actuator 113.

The console 102 can be configured to control, monitor, supply, or otherwise support operation of the treatment device 110. For example, the console 102 can include an energy generator operably connected to the neuromodulation element(s) 126 and configured to generate a selected form and magnitude of therapeutic, neuromodulation energy (e.g., radiofrequency energy ("RF"), pulsed energy, microwave energy, optical energy, direct heat energy, or another suitable type of energy) for delivery to the treatment site via the neuromodulation element(s) 126 to alter, damage, or disrupt nerves.

In some embodiments, the console 102 can be configured to store and/or transmit (via the connector 101 and/or the elongated shaft 112) irrigation fluid (e.g., saline, distilled water, etc.) to the treatment assembly 120. As noted previously, for example, the console 102 includes the irrigation pump 104 to transfer irrigation fluid from the console 102 to the treatment assembly 120 of the treatment device 110. In other embodiments, the system 100 can include a neuromodulation console (not shown) and a separate irrigation console (not shown) containing the irrigation pump 104 and/or a storage container (not shown) to store irrigation fluid. In these embodiments, the neuromodulation console can be communicatively coupled to the irrigation console. As described in greater detail below, the system 100 can facilitate simultaneous and/or coordinated delivery of neuromodulation energy and irrigation fluid to the treatment assembly 120. To reduce the likelihood of tissue damage and/or associated adverse effects, the irrigation fluid can be used to cool (i) tissue at the treatment site and/or (ii) components of the treatment assembly 120.

The console 102 can be electrically coupled to the treatment device 110 via the connector 101 (e.g., a cable). One or more supply wires (not shown) can pass along the elongated shaft 112 or through a lumen in the elongated shaft 112 to the neuromodulation element(s) 126 to transmit the neuromodulation energy to the neuromodulation element(s) 126. In addition, one or more fluid supply lumens (not shown) can pass along the elongated shaft 112 or through a lumen in the elongated shaft 112 to the treatment assembly 120. The fluid supply lumen(s) can transmit irrigation fluid to one or more irrigation outlets (not shown) in the treatment assembly 120.

The console 102 can also be configured to deliver neuromodulation energy and/or irrigation fluid to the treatment assembly 120 in accordance with an automated control algorithm 150 and/or under the control of a clinician. The control algorithm 150 may be executed on a processor (not shown) of the system 100. One or more sensors (e.g., pressure, temperature, impedance, flow, chemical, ultrasound, electromagnetic, etc.) of the treatment assembly 120 and/or of the treatment device 110 can generate diagnostic information/measurements regarding patient tissue at the treatment site and/or regarding components of the treatment assembly 120. The diagnostic information can be used as feedback for the control algorithm 150 and can allow the system 100 to adjust the control algorithm 150 (e.g., based on a comparison of the diagnostic information to predetermined parameter profile ranges). In particular, the system 100 can adjust characteristics (e.g., type, power level, duration, frequency, etc.) of neuromodulation energy delivered to the neuromodulation element(s) 126 and/or characteristics (e.g., volume, temperature, type, rate, duration, etc.) of irrigation fluid delivered to the treatment assembly 120. The diagnostic information can also provide feedback to the clinician, such as via an indicator 105 (e.g., a display, a user interface, one or more LEDs, etc.) associated with the console 102 and/or the system 100. For example, the console 102 may include a user interface that can receive user input and/or provide the diagnostic information to the user. The feedback from the diagnostic information can allow a clinician to determine the effectiveness of the applied energy during the treatment and/or shortly thereafter (e.g., while the patient is still catheterized). Likewise, while the patient is still catheterized, a clinician may decide to repeat, pause, and/or terminate treatment based on feedback from the diagnostic information (e.g., to avoid tissue damage). Accordingly, this feedback may be useful in helping the clinician increase the likelihood of success of the current or subsequent treatments and/or avoid adverse effects of the treatment(s). Further details regarding a suitable control algorithm 150 are described below with reference to FIG. 5.

The system 100 can include a controller 106 having, for example, memory (not shown), storage devices (e.g., disk drives), one or more output devices (e.g., a display), one or more input devices (e.g., a keyboard, a touchscreen, etc.), and/or processing circuitry (not shown). The controller 106 can be configured to execute, adjust, and/or modify the control algorithm 150. For example, the output devices may be configured to communicate with the treatment device 110 (e.g., via the connector 101) to control power to the neuromodulation element(s) 126 and/or to control supply of irrigation fluid to the treatment assembly 120. In some embodiments the output devices can further be configured to obtain signals from the neuromodulation element(s) 126 and/or any associated sensors. Display devices may be configured to provide indications of power levels or sensor data, such as audio, visual, or other indications, and/or the display devices may be configured to communicate the information to another device.

In some embodiments, the controller 106 can be part of the console 102, as shown in FIG. 1. Additionally or alternatively, the controller 106 can be personal computer(s), server computer(s), handheld or laptop device(s), multiprocessor system(s), microprocessor-based system(s), programmable consumer electronic(s), digital camera(s), network PC(s), minicomputer(s), mainframe computer(s), tablets, and/or any suitable computing environment. The memory and storage devices are computer-readable storage media that may be encoded with non-transitory, computer-executable instructions (e.g., the control algorithm 150, the feedback algorithm(s), etc.). In addition, the instructions, data structures, and message structures may be stored or transmitted via a data transmission medium, such as a signal on a communications link and may be encrypted. Various communication links may be used, such as the Internet, a local area network, a wide area network, a point-to-point dial-up connection, a cell phone network, Bluetooth, RFID, and other suitable communication channels. The system 100 may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

The neuromodulation element(s) 126 of the treatment assembly 120 can be configured to modulate one or more nerves (e.g., renal nerves) within tissue at or at least proximate to a wall of a vessel or lumen. As described in greater detail below, the neuromodulation element(s) 126 can include one or more energy delivery elements (e.g., electrodes; FIGS. 2A-4) and/or one or more sensors (e.g., to monitor the energy delivery elements and/or tissue at the treatment site). For example, in some embodiments, the neuromodulation element(s) 126 can include a single energy delivery element located at a distal portion 116 of the treatment device 110. In other embodiments, the neuromodulation element(s) 126 can include two or more energy delivery elements. The energy delivery elements can be separate band electrodes spaced apart from each other along a portion of the length of the shaft 112. The electrodes can be adhesively bonded to a support structure at different positions along the length of the shaft 112. In some embodiments, the energy delivery elements can be formed from a suitable electrically conductive material (e.g., a metal, such as gold, platinum, alloys of platinum and iridium, etc.). The number, arrangement, shape (e.g., spiral and/or coil electrodes) and/or composition of the energy delivery elements may vary. The individual energy delivery elements of the neuromodulation element(s) 126 can be electrically connected to the handle assembly 111 and/or the console 102 by a conductor or bifilar wire extending through a lumen of the shaft 112.

In embodiments having multiple energy delivery elements, the energy delivery elements may deliver power independently (e.g., may be used in a monopolar fashion), either simultaneously, selectively, or sequentially, and/or may deliver power between any desired combination of the elements (e.g., may be used in a bipolar fashion). Furthermore, the clinician optionally may be permitted to choose which energy delivery element(s) are used for power delivery in order to form highly customized lesion(s) within the vessel (e.g., the renal artery) or other body lumens (e.g., the ureter), as desired. In some embodiments, the system 100 may be configured to provide delivery of a monopolar electric field via the neuromodulation element(s) 126. In such embodiments, a neutral or dispersive electrode 109 may be electrically connected to the console 102 and attached to the exterior of the patient.

Figure 2A:
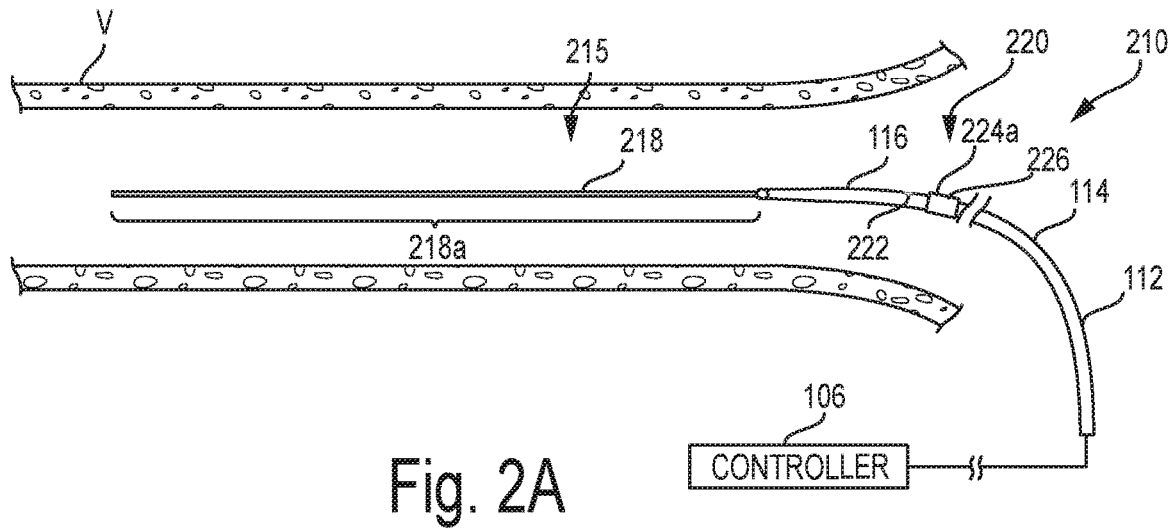
FIG. 2A is a partially schematic side view of a neuromodulation catheter with a distal portion of a guidewire positioned within a blood vessel of a human patient and configured in accordance with an embodiment of the present technology.
Figure 2B:
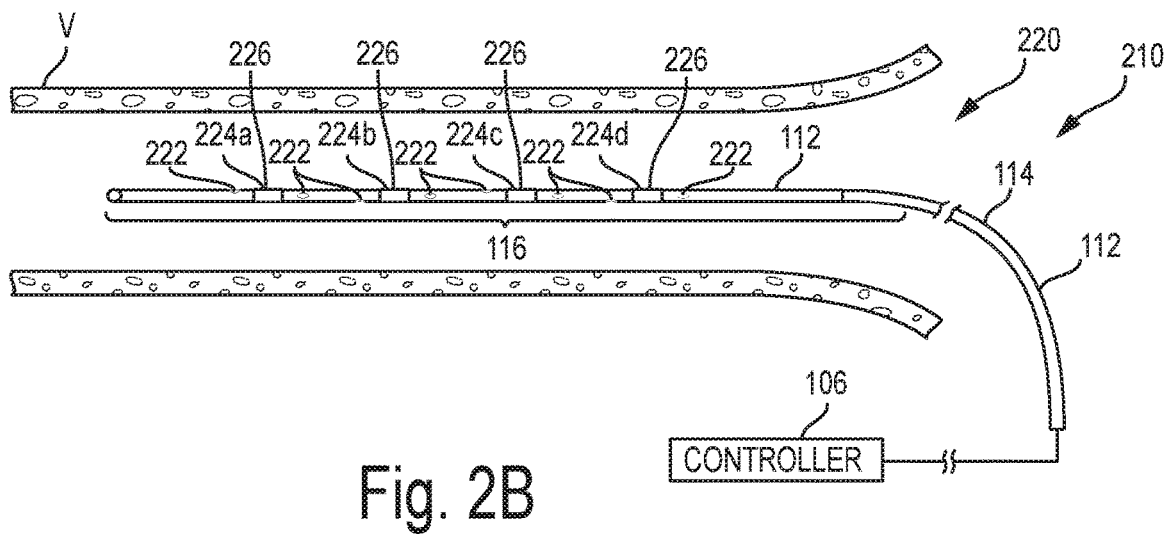
FIGS. 2B and 2C are partially schematic side views of the neuromodulation catheter shown in FIG. 2A with an irrigated treatment assembly in a first state and a second state, respectively, within the blood vessel of the human patient.
Figure 2C:
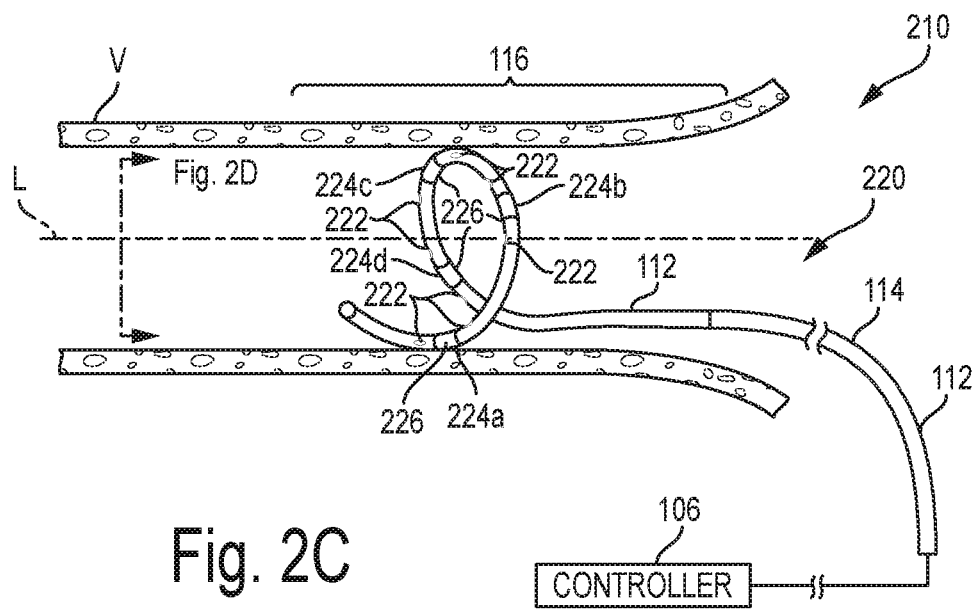

FIGS. 2A-2C are partially schematic side views of a neuromodulation catheter 210 (e.g., the treatment device 110 shown in FIG. 1) configured in accordance with an embodiment of the present technology. The neuromodulation catheter 210 is shown in different arrangements in FIGS. 2A-2C while positioned at a treatment site within a blood vessel V (e.g., a renal artery) of a human patient. The neuromodulation catheter 210 includes a guidewire 215 (only visible in FIG. 2A) and an irrigated treatment assembly 220 that can be advanced over the guidewire 215 to the treatment site within the blood vessel V. The irrigated treatment assembly 220 is configured to perform neuromodulation therapy at the treatment site to, for example, ablate nerves proximate the wall of the blood vessel V. As discussed in greater detail below, the irrigated treatment assembly 220 can be configured to monitor tissue of the blood vessel V at the treatment site and components (e.g., neuromodulation element(s) 226) of the irrigated treatment assembly 220. For example, one or more sensors (not shown) of the irrigated treatment assembly 220 are configured to gather diagnostic information and measurements relating to the temperature of the tissue and/or the neuromodulation element(s) 226 during neuromodulation treatment of the tissue. The diagnostic information can be used as feedback to adjust characteristics of neuromodulation energy delivery and/or characteristics of irrigation fluid delivery to the irrigated treatment assembly 220.

The guidewire 215 includes an elongated member 218 having a distal portion 218a configured to be positioned at the treatment site within the blood vessel V and a proximal portion (not visible) that extends outside of the patient to a handle (e.g., the handle 111 shown in FIG. 1) or other feature(s) that allow an operator to manipulate the distal portion 218a to the desired position/orientation (e.g., using the actuator 113 shown in FIG. 1). The elongated member 218 can be sized to be slidably positioned within a lumen of the neuromodulation catheter 210. In other embodiments, the elongated member 218 comprises other suitable components (e.g., sensor(s)) and/or configurations. Additionally, the elongated member 218 can have a uniform stiffness along its length, or can have a stiffness that varies along its length.

As best shown in FIG. 2B, the elongated shaft 112 of the neuromodulation catheter 210 is configured to be slidably delivered over the guidewire 215. The elongated shaft 112 has a distal portion 116 configured to be intravascularly positioned at the treatment site within the blood vessel V and a proximal portion 114 extending outside of the patient to a handle (e.g., the handle 111 shown in FIG. 1) or other features that allow an operator to manipulate the distal portion 116 of the elongated shaft 112 (e.g., using the actuator 113 shown in FIG. 1). As shown in FIGS. 2B and 2C, for example, the irrigated treatment assembly 220 of the neuromodulation catheter 210 is transformable between a first state or arrangement in which the distal portion 116 of the elongated shaft 112 is at least generally straight low-profile delivery arrangement (FIG. 2B), and a second (e.g., deployed, expanded, etc.) state or arrangement in which the distal portion 116 is transformed or otherwise expanded to a spiral/helical shape (FIG. 2C). In some embodiments, the treatment assembly 220 can have a shape memory corresponding to the second state, and the guidewire 215 (FIG. 2A) can retain the treatment assembly 220 in the first state until the guidewire 215 is at least partially removed (e.g., withdrawn). The dimensions (e.g., outer diameter and length) of the distal portion 116 of the elongated shaft 112 (e.g., the portion that takes on the spiral/helical shape in the second state illustrated in FIG. 2C) can be selected to accommodate the vessels or other body lumens in which the distal portion 116 is designed to be delivered. For example, when in the second state, the axial length of the distal portion 116 of the elongated shaft 112 may be selected to be no longer than a patient's renal artery (e.g., typically less than 7 cm), and have a diameter that accommodates the inner diameter of a typical renal artery (e.g., about 2-10 mm). In other embodiments, the distal portion 116 of the elongated shaft 112 can have other dimensions depending on the body lumen within which it is configured to be deployed. In other embodiments, the distal portion 116 of the elongated shaft 112 can have other suitable shapes (e.g., semi-circular, curved, straight, etc.), sizes, and/or configurations. Other suitable devices and technologies are described in, for example, U.S. Pat. Nos. 8, 777,942; 9,084,610; 9,060,755; 8,998,894; PCT Application No. PCT/US2011/057754, filed Oct. 25, 2011; and U.S. Pat. No. 8,888,773. All of the foregoing applications are incorporated herein by reference in their entireties. One non-limiting example of a device and system includes the Symplicity Spyral™ multielectrode RF ablation catheter.

Referring to FIGS. 2B and 2C together, the irrigated treatment assembly 220 includes four neuromodulation elements 226 spaced along the distal portion 116 of the elongated shaft 112. In other embodiments, however, the irrigated treatment assembly 220 may include one, two, three, or more than four neuromodulation element(s) 226 and/or may include multiple support members configured to carry one or more neuromodulation elements 226. Each neuromodulation element 226 in the illustrated embodiment includes an electrode 224 (identified individually as first through fourth electrodes 224a-224d, respectively). Neuromodulation elements 226 in other embodiments can include a greater and/or lesser number of electrodes 224. In some embodiments, the neuromodulation elements 226 can include one or more sensors configured to monitor tissue at the treatment site and/or components (e.g., the electrodes 224a-224d) of the treatment assembly 220.

The electrodes 224a-224d are configured to deliver neuromodulation energy (e.g., RF energy) to tissue at or at least proximate to the vessel wall V at the treatment site to modulate one or more nerves (e.g., renal nerves) within the tissue when the irrigated treatment assembly 220 is in the second state illustrated in FIG. 2C. In this state, the distal portion 116 of the elongated shaft 112 may be designed to apply a desired outward radial force to the blood vessel V to place one or more of the electrodes 224a-224d in contact with the vessel wall. In these and other embodiments, the irrigated treatment assembly 220 can include electrodes, transducers, or other elements to deliver other suitable neuromodulation modalities, such as pulsed electrical energy, microwave energy, optical energy, ultrasound energy (e.g., intravascularly delivered ultrasound and/or high-intensity focused ultrasound (HIFU)), direct heat energy, radiation (e.g., infrared, visible, and/or gamma radiation), and/or other suitable types of energy to alter, damage, or disrupt nerves.

As explained above, the treatment assembly 220 and/or one or more of the neuromodulation elements 226 can include one or more sensors (not shown) configured to monitor characteristics of tissue, such as temperature, at the treatment site and/or of components (e.g., the electrodes 224a-224d and/or the neuromodulation element(s) 226) of the treatment assembly 220. In some embodiments, the one or more sensors can be directly incorporated into the neuromodulation element(s) 226 (e.g., into and/or proximal to the electrodes 224a-224d) of the irrigated treatment assembly. In these and other embodiments, the one or more sensors can be located at various locations along the elongated shaft 112 of the neuromodulation catheter 210 and/or apart from the neuromodulation element(s) 226 of the irrigated treatment assembly 220. The one or more sensors can be configured to measure and/or generate diagnostic information regarding tissue of the blood vessel V and/or components of the neuromodulation element(s) 226 of the irrigated treatment assembly 220. For example, the one or more sensors can continuously and/or periodically measure temperature, pressure, time, impedance, power, flow velocity, volumetric flow rate, blood pressure, heart rate, parameters of return energy, or other parameters of the neuromodulation catheter 210 and/or patient tissue at the treatment site. Through these measurements, the one or more sensors generate diagnostic information that can be reported back to one or more controller(s) 106 of the system 100, as described in greater detail below.

As best shown in FIGS. 2B and 2C, the irrigated treatment assembly 220 can include one or more irrigation outlets 222 at the distal portion 216 of the elongated shaft 112. The irrigation outlets 222 can be connected to one or more fluid supply lumens (not shown) that extend along the elongated shaft 112 (or through a lumen in the elongated shaft 112) to an irrigation pump (e.g., the irrigation pump shown in FIG. 1) and/or a storage container (not shown). As explained above, irrigation fluid (e.g., saline, distilled water, etc.) can be transmitted via the fluid supply lumens to the treatment assembly 220 and can be released at the treatment site via the irrigation outlets 222. In this manner, the neuromodulation catheter 210 can cool components (e.g., the neuromodulation element(s) 226) of the irrigated treatment assembly 220 and/or tissue at the treatment site (e.g., during neuromodulation treatment).

Figure 2D:
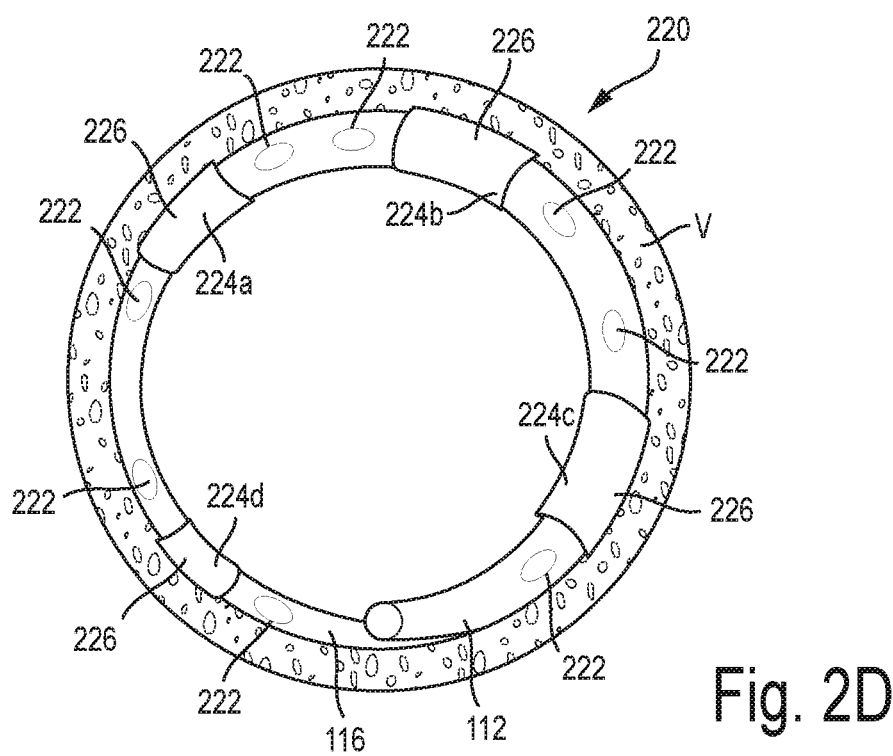
FIG. 2D is a front view of the irrigated treatment assembly in the second state shown in FIG. 2C looking proximally down a longitudinal axis of the blood vessel of the human patient.

The irrigation outlets 222 can be arranged at various points around the circumference of the elongated shaft 112 (as best shown in FIG. 2B) such that the irrigation outlets 222 are positioned in a desired orientation when the treatment assembly 220 is in the second state (shown in FIG. 2C). For example, the irrigation outlets 222 can be arranged such that they direct irrigation fluid distally along or generally along a longitudinal axis L of the blood vessel V (as shown in FIGS. 2C and 2D). In other embodiments, the irrigation outlets 222 can be oriented to face in one or more different directions (e.g., to face in a direction opposite the direction illustrated in FIGS. 2C and 2D, to face the vessel wall, and/or to face toward the center of the blood vessel V) when the treatment assembly 220 is in the second state. In operation, the system 100 can release irrigation fluid proximal to the wall of the blood vessel V and/or proximal to the electrodes 224a-224d via the irrigation outlets 222. Irrigation fluid released from an irrigation outlet 222 thus can provide cooling to (i) tissue of the vessel wall and/or (ii) components of the treatment assembly 220 near the irrigation outlet 222. In addition, irrigation fluid released from the irrigation outlets 222 can be carried along the vessel wall by blood flowing through the blood vessel V. Therefore, irrigation fluid released from an irrigation outlet 222 can also provide cooling to (i) tissue of the vessel wall, (ii) components of the treatment assembly 220, and/or (iii) components of the neuromodulation catheter 210 located downstream from the irrigation outlet 222.

Figure 3:
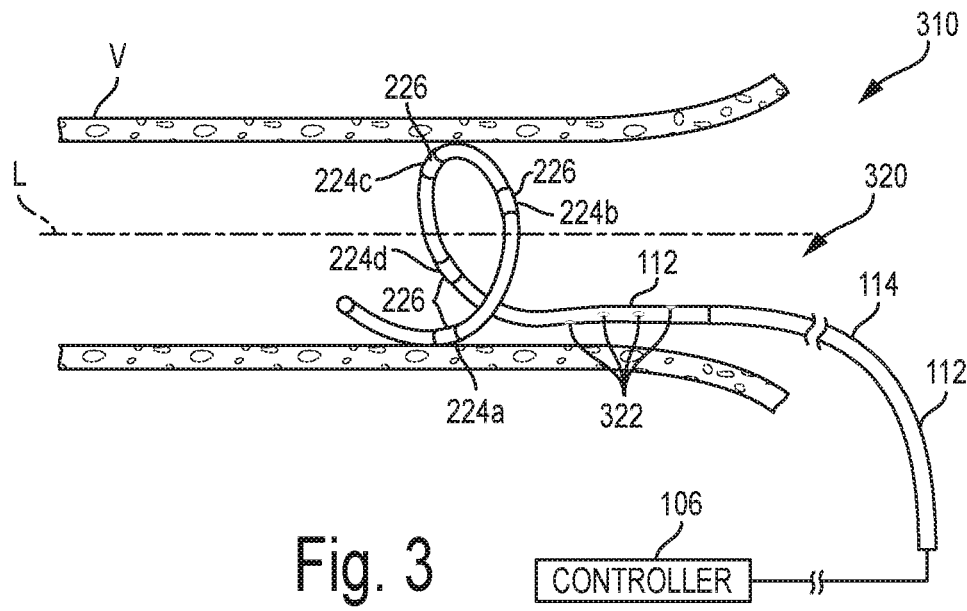
FIG. 3 is a partially schematic side view of a neuromodulation catheter having an irrigated treatment assembly in a deployed state within a blood vessel of a human patient and configured in accordance with an embodiment of the present technology.
Figure 4:
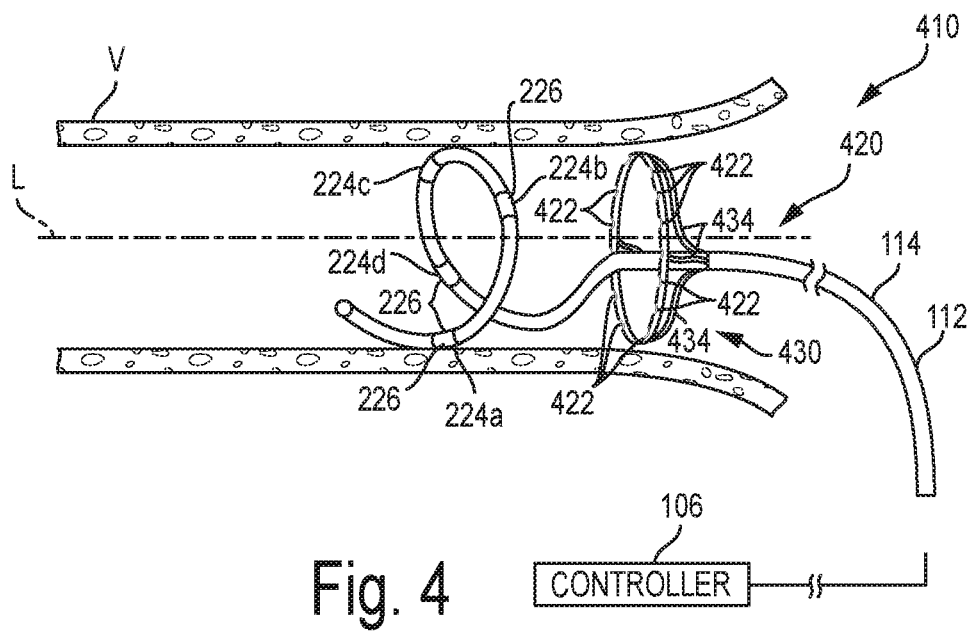
FIG. 4 is a partially schematic side view of a neuromodulation catheter having an irrigated treatment assembly in a deployed state within a blood vessel of a human patient and configured in accordance with an embodiment of the present technology.

Although the irrigation outlets 222 illustrated in FIGS. 2A-2D are positioned proximal to the electrodes 224a-224d of the treatment assembly 220, one or more of the irrigation outlets 222 can be positioned at other locations and/or in different arrangements in other embodiments of the present technology. For example, FIGS. 3 and 4 are partially schematic side views of neuromodulation catheters 310 and 410, respectively, configured in accordance with other embodiments of the present technology. As shown in FIG. 3, the neuromodulation catheter 310 includes an irrigated treatment assembly 320 having irrigation outlets 322 (e.g., the irrigation outlets 222 shown in FIGS. 2A-2D) at locations along the elongated shaft 112 that are more proximal to the proximal portion 114 of the elongated shaft 112 than the locations of the irrigation outlets 222 illustrated in FIGS. 2A-2D. The irrigation outlets 322 are positioned about the circumference of the elongated shaft 112 and are configured to release irrigation fluid radially outward from the elongated shaft 112. Additionally or alternatively, the irrigation outlets 322 can be shaped and/or fluid supply lumens coupled to the irrigation outlet(s) 322 can be oriented within the elongated shaft 112 such that irrigation fluid is output from the irrigation outlets 322 in a desired direction away from the irrigation outlets 322.

In other embodiments and as shown in FIG. 4, the neuromodulation catheter 410 can include an irrigated treatment assembly 420 having an irrigation ring/donut element 430 with one or more irrigation outlets 422. The irrigation ring element 430 is configured to expand radially outward from the elongated shaft 112 such that the irrigation ring 430 surrounds the elongated shaft 112 and is proximal to or engages an inner vessel wall. As shown, one or more fluid supply lumens 434 can extend (e.g., from the elongated shaft 112) into the irrigation ring element 430. The irrigation outlets 422 and/or the fluid supply lumens 434 can be (i) oriented to direct irrigation fluid down a longitudinal axis L of the blood vessel V, (ii) oriented to face the vessel wall and/or another direction, (iii) configured to direct irrigation toward the vessel wall, and/or (iv) shaped and/or oriented within the irrigation ring element 430 such that irrigation fluid is output from the irrigation ring element 430 in a desired direction away from the irrigation outlets 422.

As discussed above, neuromodulation catheters 210, 310, and 410 configured in accordance with embodiments of the present technology can be communicatively coupled to one or more controller(s) 106 of the console 102 (FIG. 1) via a wired or wireless communication link. In some embodiments, one or more of the controller(s) 106 may be separate from the console, such as in embodiments where the irrigation pump 104 shown in FIG. 1 is separate from the console 102. The controller(s) 106 can be configured to initiate, terminate, and/or adjust operation of one or more components (e.g., the electrodes 224a-224d) of the treatment assemblies 220, 320, and 420 directly and/or via the console 102. For example, the controller(s) 106 may be configured to continuously or intermittently monitor tissue of the blood vessel wall and/or components of the treatment assemblies 220, 320, and 420 using diagnostic information from the one or more sensors (not shown) of the treatment assemblies 220, 320, and 420. More specifically, the controller 106 can use the diagnostic information to adjust (i) characteristics of the neuromodulation energy and/or (ii) characteristics of irrigation fluid delivered to the treatment assemblies 220, 320, and 420 (e.g., in accordance with a control algorithm). Thus, the controller(s) 106 can be configured to control, monitor, supply, adjust, and/or otherwise support operation of the neuromodulation catheters 210, 310, and 410 based at least in part on the diagnostic information generated by the one or more sensors of the treatment assemblies 220, 320, and 420.

B. Control of Applied Energy and Irrigation Characteristics

Figure 5:
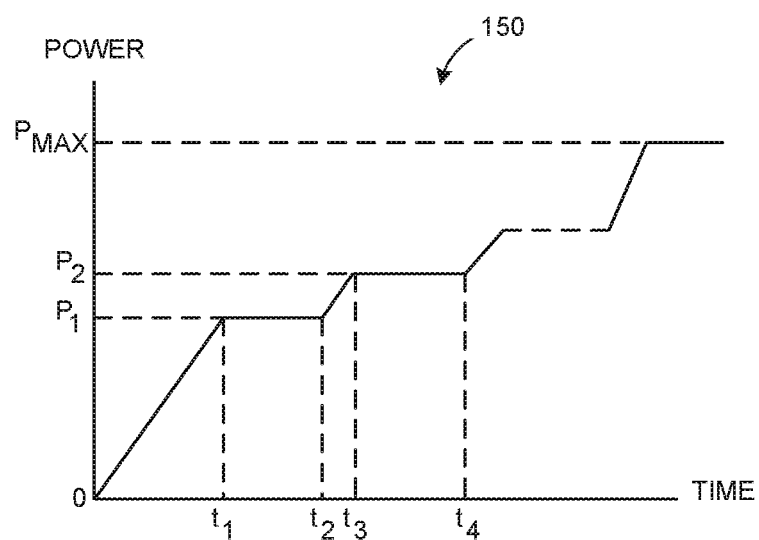
FIG. 5 is a graph depicting an energy delivery algorithm that may be used in conjunction with neuromodulation systems configured in accordance with embodiments of the present technology.

As discussed above, neuromodulation systems (e.g., the system 100 shown in FIG. 1) configured in accordance with embodiments of the present technology can be configured to deliver coordinated neuromodulation energy (e.g., RF energy) and irrigation fluid to a treatment assembly of a treatment device in accordance with an automated control algorithm 150 and/or under the control of a clinician. FIG. 5 shows one embodiment of an automated control algorithm 150 that may be implemented by a controller 106 (e.g., the controller 106 shown in FIGS. 1-4). As shown in FIG. 5, when a clinician initiates treatment, the control algorithm 150 can include instructions that cause a console (e.g., the console 102 shown in FIG. 1) to gradually adjust the power of energy applied to a treatment site to a first power level $P_1$ (e.g., 5 watts) over a first time period $t_1$ (e.g., 15 seconds). The power can increase generally linearly during the first time period. As a result, the console can increase its power output at a generally constant rate of $P_1/t_1$. Alternatively, the power may increase non-linearly (e.g., exponential or parabolic) with a variable rate of increase.

Additionally or alternatively, the control algorithm 150 can include instructions that coordinate delivery of irrigation fluid to the treatment site before, during, and/or after neuromodulation energy is applied to the treatment site, adjusted, and/or modified. For example, the control algorithm 150 can include instructions that direct the system (e.g., a console and/or an irrigation pump) to deliver irrigation fluid with characteristics corresponding to the increase in power to the first power level $P_1$. In some embodiments, the instructions can direct the system to deliver a specific type (e.g., saline, distilled water, etc.) and/or volume of irrigation fluid to the treatment site. In these and other embodiments, the instructions can direct the system to (i) deliver irrigation fluid at a specified temperature (e.g., room temperature, body temperature, or another temperature above or below room temperature), (ii) deliver irrigation fluid at a specified flow rate, and/or (ii) deliver irrigation fluid for a specified duration. In these and still other embodiments, instructions can direct the system to adjust (e.g., increase, decrease, change, and/or terminate) any of these irrigation fluid characteristics as the power is adjusted (e.g., increased, decreased, and/or held constant). In still other embodiments, the control algorithm 150 can include instructions to refrain from delivering irrigation fluid until a specified power level is reached, a specified electrode temperature is reached, and/or for a specified period of time.

Once $P_1$ and $t_1$ are achieved, the control algorithm 150 may hold at $P_1$ until a new time $t_2$ for a predetermined period of time $t_2-t_1$ (e.g., 3 seconds). The control algorithm 150 may similarly hold the irrigation fluid characteristics constant until $t_2$ and/or may adjust the irrigation fluid characteristics (e.g., based on monitored parameters of the tissue at the treatment site and/or of components of the treatment device, as described in greater detail below). At $t_2$, power is increased by a predetermined increment (e.g., 1 watt) to $P_2$ over a predetermined period of time, $t_3-t_2$ (e.g., 1 second). The control algorithm 150 can include instructions directing the system to adjust irrigation fluid characteristics in accordance with this power increase. The power ramp in predetermined increments of about 1 watt over predetermined periods of time may continue until a maximum power $P_{MAX}$ is achieved or some other condition is satisfied (e.g., a maximum irrigation flow rate/volume and/or a minimum irrigation fluid temperature is reached). Optionally, the power may be maintained at the maximum power $P_{MAX}$ for a desired period of time or up to the desired total treatment time (e.g., up to about 120 seconds). In these and other embodiments, the controller can continually change the irrigation fluid characteristics based on, for example, (i) monitored parameters of the tissue at the treatment site and/or of the components of the treatment device and/or (ii) the progress of the neuromodulation procedure.

Furthermore and before, during, and/or after the neuromodulation procedure, the controller can monitor (e.g., using one or more sensors of the treatment assembly) one or more parameters corresponding to tissue at the treatment site, to the patient, to the irrigation fluid, and/or to components (e.g., neuromodulation elements) of a treatment device. For example, the controller can continuously or periodically monitor temperature, time, impedance, power, flow velocity, volumetric flow rate, blood pressure, heart rate, parameters of return energy, and/or other parameters. The controller can use diagnostic information/measurements of the parameters as feedback regarding the progress of the neuromodulation procedure, the state (e.g., temperature) of treatment device components, and/or of the condition of the tissue at the treatment site. In some embodiments, the controller (i) can check the monitored parameters against predetermined parameter profiles to determine whether the parameters individually or in combination fall within the ranges set by the predetermined parameter profiles, and (ii) can accordingly coordinate and/or adjust characteristics of the neuromodulation energy and/or of irrigation fluid delivered to the treatment site. For example, the controller can check whether the monitored parameters fall within ranges set by the predetermined parameter profiles given certain neuromodulation energy characteristics and/or irrigation fluid characteristics. If the monitored parameters fall within the ranges, then treatment may continue in accordance with the control algorithm 150. If the monitored parameters fall outside the ranges, however, the controller can adjust the control algorithm 150 accordingly.

For example, if temperature measurements relating to the tissue at the treatment site and/or to components (e.g., the neuromodulation elements) of the treatment device are too high for a currently applied power level, the controller can adjust and/or modify the control algorithm 150 (e.g., until the parameters are within the parameter profile range(s)). In some embodiments, the controller can decrease, pause, and/or terminate the applied power; can lengthen or shorten $t_1$, $t_2$, $t_3$, etc. of the control algorithm 150; and/or can modify the duty cycle, frequency, or other parameters of the control algorithm 150. Additionally or alternatively, the controller can change characteristics of the irrigation fluid delivered to the treatment site. For example, the controller can increase and/or decrease the flow rate of, the volume of, and/or the temperature of the irrigation fluid delivered to the treatment site. In these and other embodiments, the controller can change the type of irrigation fluid released at the treatment site and/or the duration for which irrigation fluid is applied to the treatment site. It will be appreciated by those skilled in the art that the controller can adjust (e.g., increase, decrease, alter, adjust, and/or otherwise change) or hold constant the control algorithm 150 in response to other events noted by the control algorithm 150. For example, the controller can appropriately adjust the control algorithm 150 in response to (i) one or more parameters outside of (e.g., above and/or below) predetermined parameter profile range(s); and/or (ii) a sudden, unexpected, and/or undesired change in measured parameters/characteristics of the tissue and/or of the components of the treatment device (e.g., even when the parameters/characteristics fall within the parameter profile range(s)). The system may also be equipped with various audible and visual alarms to allow the controller to alert the operator of certain conditions.

In some embodiments, the system can include one or more safety thresholds that prevent the controller from adjusting characteristics of the energy and/or of the irrigation fluid above and/or below the thresholds. For example, while the neuromodulation energy is applied at or above a specified power level and/or for longer than a specified duration, the system can prevent the controller from (i) decreasing the flow rate below a specified threshold and/or (ii) increasing the temperature of the irrigation fluid above a specified threshold. In other embodiments, to prevent the system (e.g., one or more sensors on neuromodulation elements of the treatment device) from reporting an inaccurate (e.g., temperature) measurement regarding components of the treatment device and/or the tissue at the treatment site, the system can prevent the controller from (i) increasing the flow rate of the irrigation fluid above a specified threshold and/or (ii) decreasing the temperature of the irrigation fluid below a specified threshold. In still other embodiments, the system can prevent the controller from increasing the power level of the neuromodulation energy above a specified threshold (e.g., when the maximum flow rate and/or volume of irrigation fluid supplied to the treatment site is reached and/or when the minimum temperature of irrigation fluid is reached).

In this manner, the controller can deliver coordinated neuromodulation energy and irrigation fluid to the treatment site. As a result, the controller can hold the temperature of the neuromodulation elements constant and/or within a desired range through controlled and/or continued use of irrigation fluid having desired characteristics. This permits the neuromodulation system to achieve greater lesion depths by increasing the power of the neuromodulation energy applied to the blood vessel without coagulation of blood or charring of the vessel tissue associated with elevated electrodes temperatures during therapy. The maximum power that can safely be delivered to the patient during therapy is therefore increased. In particular, neuromodulation systems configured in accordance with the present technology permit power to be safely increased until a maximum power level of the energy generator is achieved, until a maximum irrigation flow rate/volume is achieved, until a minimum irrigation fluid temperature is achieved, and/or until the system otherwise prevents the controller from increasing the power further (e.g., in accordance with preset safety thresholds). In some embodiments, the maximum irrigation flow rate and/or volume can be determined by (i) irrigation pump capacity; (ii) a patient's blood dilution limit (ensuring adequate blood supply to an end-organ); (iii) safety factors determined from pre-clinical models, general human anatomical knowledge, specific patient anatomy, and/or ablation location; and/or (v) achievement of specific lesion depth. In addition, because irrigation fluid is applied in a controlled manner (e.g., only when needed, with desired characteristics, and/or at flow rates typically less than conventional irrigated systems) throughout the neuromodulation procedure, diagnostic information reported to the controller regarding the progress of the neuromodulation procedure, the condition of the tissue at the treatment site, and/or the condition of components of the treatment device remain meaningful and accurate. As a result, the neuromodulation system of the present technology is better able to avoid tissue damage and adverse effect of neuromodulation treatment typically noted after use of conventional neuromodulation systems.

Figure 6:
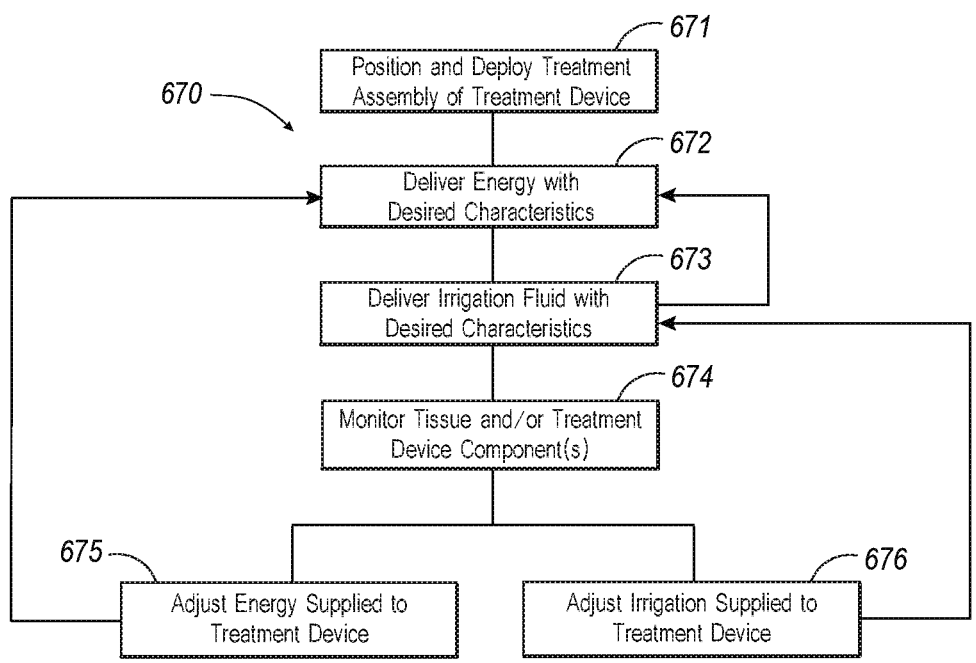
FIG. 6 is a flow diagram of a process or method for treating a patient using a neuromodulation system configured in accordance with embodiments of the present technology.

FIG. 6 is a flow diagram illustrating a routine 670 directed to a method of treating a patient configured in accordance with embodiments of the present technology. The routine 670 can be performed by, for example, various components of the neuromodulation system (e.g., a console, a controller, a control algorithm, an irrigation pump, and/or a treatment device) and/or a clinician operating the neuromodulation system. The routine 670 can begin at block 671 by positioning a treatment assembly of a treatment device intravascularly (e.g., within a renal artery) or within another suitable body lumen (e.g., within a ureter) within a patient. The routine 670 can further includes deploying the treatment assembly (e.g., by withdrawing a guidewire) at a treatment site within the patient.

At block 672, the routine 670 can include delivering neuromodulation energy via neuromodulation elements of the treatment assembly to tissue at the treatment site (e.g., in accordance with a control algorithm of the neuromodulation system). At block 673, the routine 670 can additionally or alternatively include delivering irrigation fluid having desired characteristics via irrigation outlets in the treatment assembly. Delivery of the irrigation fluid can be controlled, for example, in accordance with the control algorithm. For example, the routine 670 can (i) deliver neuromodulation energy at a first power level after and/or over a first period of time and/or (ii) deliver a first type of irrigation fluid with desired characteristics (e.g., at a first volume, temperature, and/or flow rate) corresponding to the ramp in power. In some embodiments, the routine 670 can deliver irrigation fluid having specified characteristics to hold the temperature of neuromodulation elements on the treatment assembly within a desired temperature range. In these and other embodiments, the routine 670 can refrain from delivering irrigation fluid to the treatment site until the neuromodulation energy reaches a specified power level and/or until the neuromodulation elements and/or tissue at the treatment site reach a specified temperature.

In some embodiments, the routine 670 can continue to increase the power of the neuromodulation energy and/or to modify the characteristics of the irrigation fluid delivered to the treatment site in accordance with the control algorithm. For example, the routine 670 can increase the power of the neuromodulation energy to a second power level (e.g., after a second period of time) and apply the neuromodulation energy to tissue at the treatment site at the second power level (block 672). Additionally, the routine 670 can adjust and/or modify the characteristics of the irrigation fluid delivered to the treatment site in accordance with this power increase. For example, the routine 670 can increase the volume and/or flow rate of irrigation fluid delivered to the treatment site as the power of the neuromodulation energy is increased (block 673). In these and other embodiments, the routine 670 can decrease the temperature at which the irrigation fluid is supplied to the treatment site and/or can alter the type of irrigation fluid supplied to the treatment site (block 673). In other embodiments, the routine 670 (i) can keep the irrigation fluid characteristics constant, (ii) stop delivery of irrigation fluid to the treatment site, and/or (iii) wait to adjust and/or modify the characteristics of the irrigation fluid supplied to the treatment site until the second power level is reached and/or until the neuromodulation elements reach a specified temperature (block 673).

In some embodiments, the routine 670 can continue to deliver neuromodulation energy and/or irrigation fluid in accordance with the control algorithm until a maximum power value and/or other safety thresholds of the neuromodulation system is/are reached (blocks 672 and 673). At this point, the routine 670 can prevent an increase in power if a maximum volume and/or flow rate of irrigation fluid is reached. Additionally or alternatively, the routine 670 can prevent an increase in power if a minimum temperature of irrigation fluid is reached and/or a maximum temperature of the neuromodulation elements is reached.

At any point before, during, and/or after positioning and/or deploying the treatment assembly, the routine 670 can monitor (e.g., continuously and/or simultaneously) one or more parameters relating to the patient and/or to components (e.g., neuromodulation elements and/or electrodes) of the neuromodulation system (block 674). For example, the routine 670 can use one or more sensors located on or near neuromodulation elements of the treatment device to measure the temperature, impedance, duration, power, flow velocity, volumetric flow rate, blood pressure, heart rate, parameters of return energy, and/or other parameters of the tissue at the treatment site, of the patient, of the irrigation fluid, and/or of the neuromodulation elements of the treatment device. The routine 670 can use this diagnostic information as feedback regarding the progress of a neuromodulation procedure (e.g., the size and/or depth of a lesion formed during treatment), the condition of the tissue at the treatment site, and/or the condition of components of the neuromodulation system.

In some embodiments, the routine 670 can determine whether to adjust and/or modify one or more characteristics of the neuromodulation energy applied to the treatment site and/or of the irrigation fluid supplied to the treatment site, respectively, based at least in part on the diagnostic information. For example, the routine 670 can compare the diagnostic information to predetermined parameter profile ranges to determine if one or more parameters are outside of those range(s). If specific parameters and/or a predetermined number of parameters fall within the parameter profile ranges, the routine 670 can continue to apply neuromodulation energy and/or irrigation fluid in accordance with the control algorithm (blocks 672 and/or 673).

On the other hand, if one or more of the parameters fall outside (e.g., above and/or below) the predetermined parameter profile ranges, the routine 670 can decide to adjust and/or modify one or more characteristics of the neuromodulation energy (block 675) and/or of the irrigation fluid (block 676) applied to the treatment site. For example, if the routine 670 determines the temperature of the tissue at the treatment site and/or of the neuromodulation elements is above the predetermined temperature profile range (e.g., given the current energy characteristics, the current stage in the neuromodulation procedure, the current irrigation fluid characteristics, and/or safety threshold(s)), the routine 670 can alter and/or modify the control algorithm to alter and/or modify the power level of the neuromodulation energy (block 675). In some embodiments, the routine 670 can decrease the power at which neuromodulation energy is applied. In other embodiments, the routine 670 can hold the power level constant and/or can increase the power level at a slower rate. Additionally or alternatively, the routine 670 can alter and/or modify the control algorithm to alter and/or modify the irrigation fluid characteristics (e.g., block 676). For example, the routine 670 can (i) increase the volume and/or flow rate of the irrigation fluid applied at the treatment site, (ii) decrease the temperature at which the irrigation fluid is applied at the treatment site, and/or (iii) change the type of irrigation fluid applied to the treatment site. In some embodiments, the routine 670 can (i) increase the power of the neuromodulation energy and/or the temperature of the irrigation fluid applied to the treatment site and/or (ii) decrease the volume and/or flow rate of the irrigation fluid only after the one or more parameters move back within the predetermined parameter profile range(s).

Although the steps of the routine 670 are discussed and illustrated in a particular order, the method illustrated by the routine 670 is not so limited. In other embodiments, the method can be performed in a different order. For example, one or more sensors of the neuromodulation system can monitor parameters of the neuromodulation system and/or of the patient before energy and/or irrigation fluid is delivered to the treatment site. In other embodiments, irrigation fluid can be applied to the treatment site before neuromodulation energy is applied to the treatment site and/or adjusted. In these and other embodiments, the neuromodulation system may require that an increase in power applied to the treatment site be proceeded by and/or be applied simultaneously with (i) an increase in the volume and/or flow rate of irrigation fluid applied to the treatment site and/or (ii) a decrease in the temperature of irrigation fluid. Moreover, blocks 671-676 are illustrated for the sake of completeness.

A person skilled in the art will readily recognize that the illustrated method can be altered and still remain within these and other embodiments of the present technology. For example, one or more steps of the method illustrated in FIG. 6 can be omitted and/or repeated in some embodiments.

C. Selected Examples of Neuromodulation Devices and Related Systems

Figure 7:
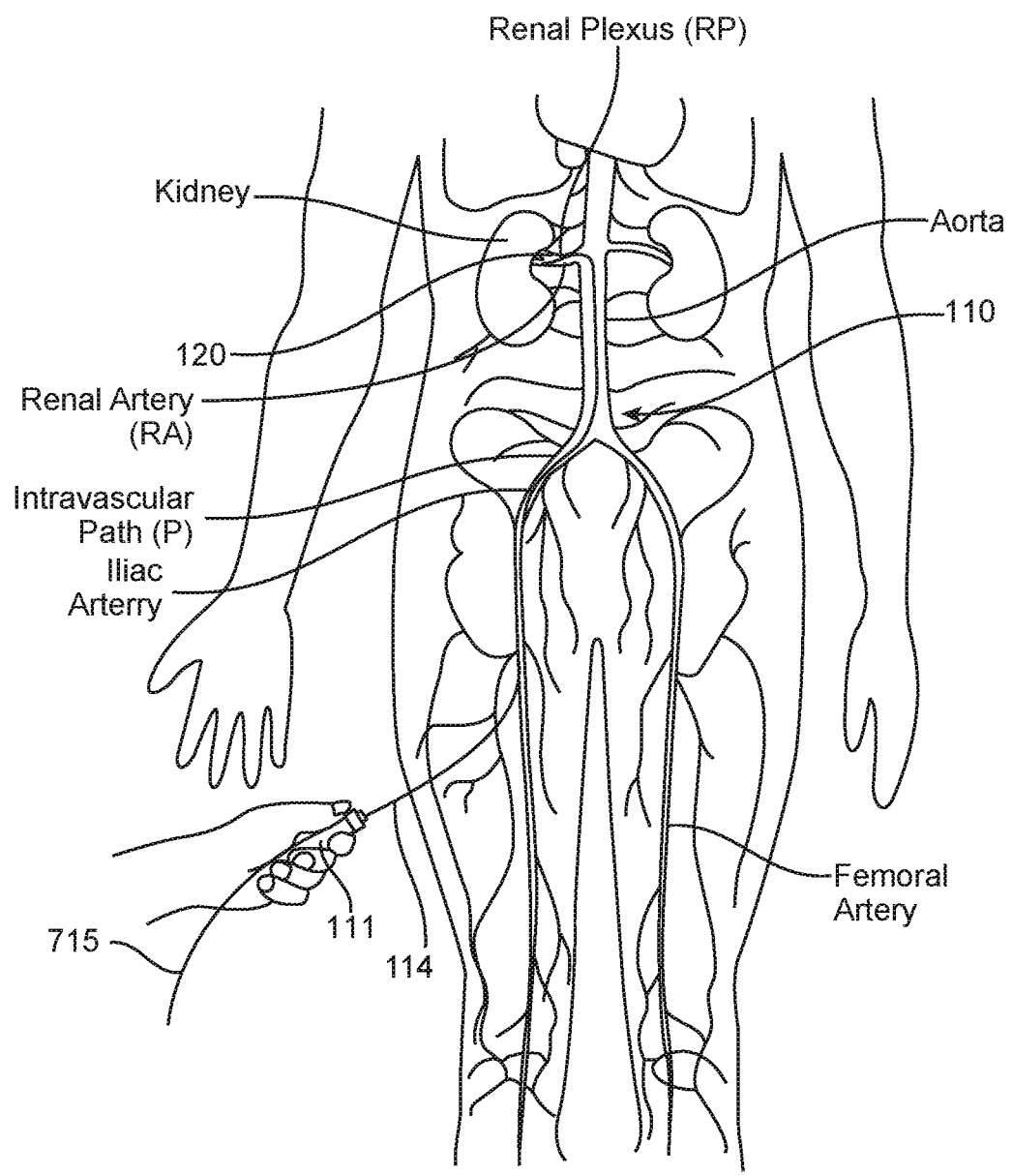
FIG. 7 illustrates modulating renal nerves and/or evaluating the neuromodulation therapy with the system of FIG. 1 in accordance with an embodiment of the present technology.

FIG. 7 (with additional reference to FIG. 1) illustrates modulating renal nerves in accordance with an embodiment of the system 100 (FIG. 1). The neuromodulation device 110 provides access to the renal plexus RP through an intravascular path P, such as a percutaneous access site in the femoral (illustrated), brachial, radial, or axillary artery to a targeted treatment site within a respective renal artery RA. By manipulating the proximal portion 114 of the elongated shaft 112 from outside the intravascular path P, a clinician may advance the elongated shaft 112 through the sometimes tortuous intravascular path P and remotely manipulate the distal portion 116 (FIG. 1) of the elongated shaft 112. In the embodiment illustrated in FIG. 7, the neuromodulation assembly 120 is delivered intravascularly to the treatment site using a guidewire 715 in an OTW technique. At the treatment site, the guidewire 715 can be at least partially withdrawn or removed, and the neuromodulation assembly 120 can transform or otherwise be moved to a deployed arrangement for recording neural activity and/or delivering energy at the treatment site. In other embodiments, the neuromodulation assembly 120 may be delivered to the treatment site within a guide sheath (not shown) with or without using the guidewire 715. When the neuromodulation assembly 120 is at the treatment site, the guide sheath may be at least partially withdrawn or retracted and the neuromodulation assembly 120 can be transformed into the deployed arrangement. In other embodiments, the elongated shaft 112 may be steerable itself such that the neuromodulation assembly 120 may be delivered to the treatment site without the aid of the guidewire 715 and/or the guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 120. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 120. Further, in some embodiments, image guidance components (e.g., IVUS, OCT) may be integrated with the neuromodulation device 110 and/or run in parallel with the neuromodulation device 110 to provide image guidance during positioning of neuromodulation assembly 120. For example, image guidance components (e.g., IVUS or OCT) can be coupled to neuromodulation assembly 120 to provide three-dimensional images of the vasculature proximate the treatment site to facilitate positioning or deploying the multi-electrode assembly within the target renal vascular structure.

Energy from the neuromodulation elements 126 may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Hypothermic effects may also provide neuromodulation. For example, a cryotherapeutic applicator may be used to cool tissue at a treatment site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

D. Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic over activity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment sites during a treatment procedure. The treatment site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

E. Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 8:
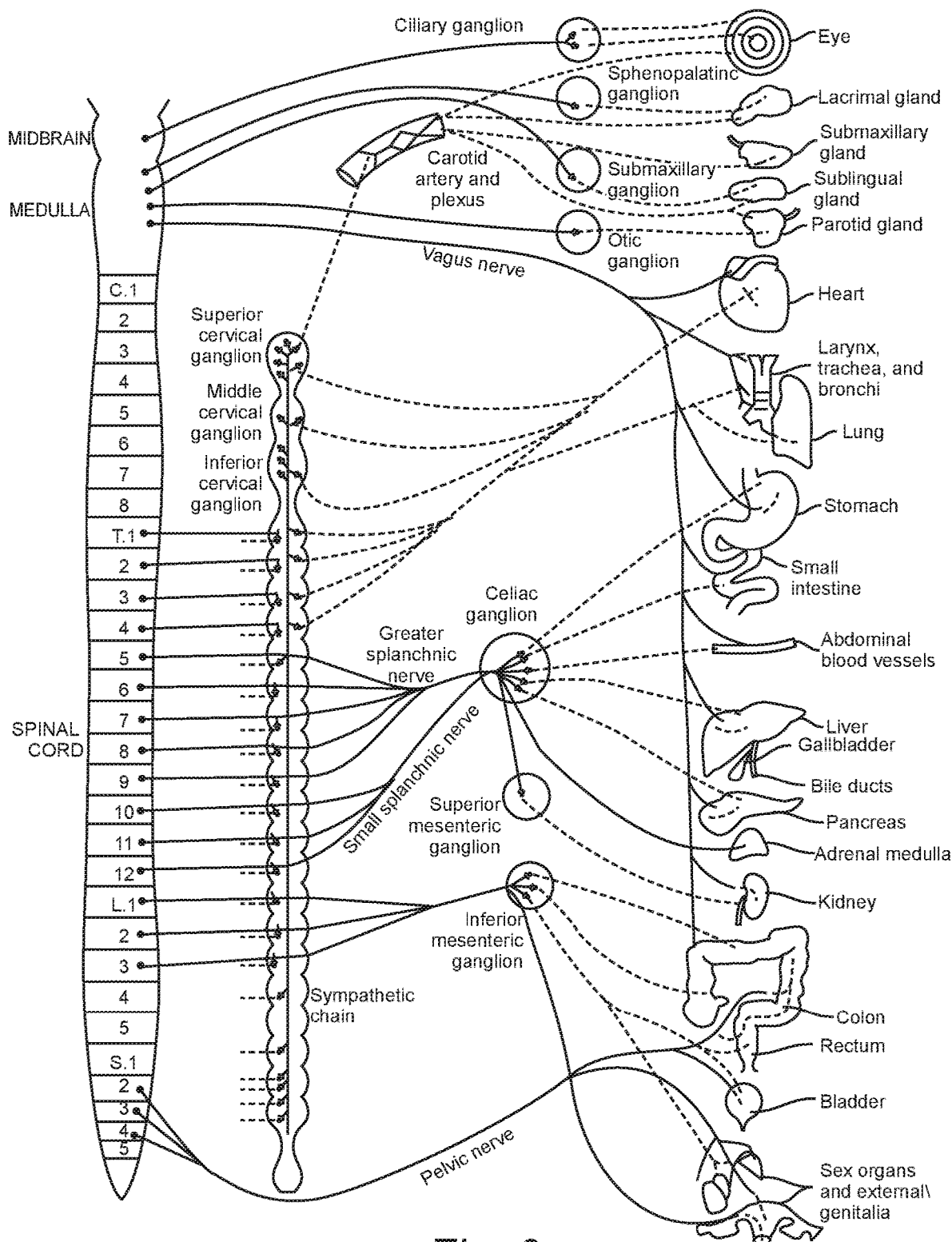
FIG. 8 is a conceptual illustration of the sympathetic nervous system (SNS) and how the brain communicates with the body via the SNS.

As shown in FIG. 8, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

a. Innervation of the Kidneys

Figure 9:
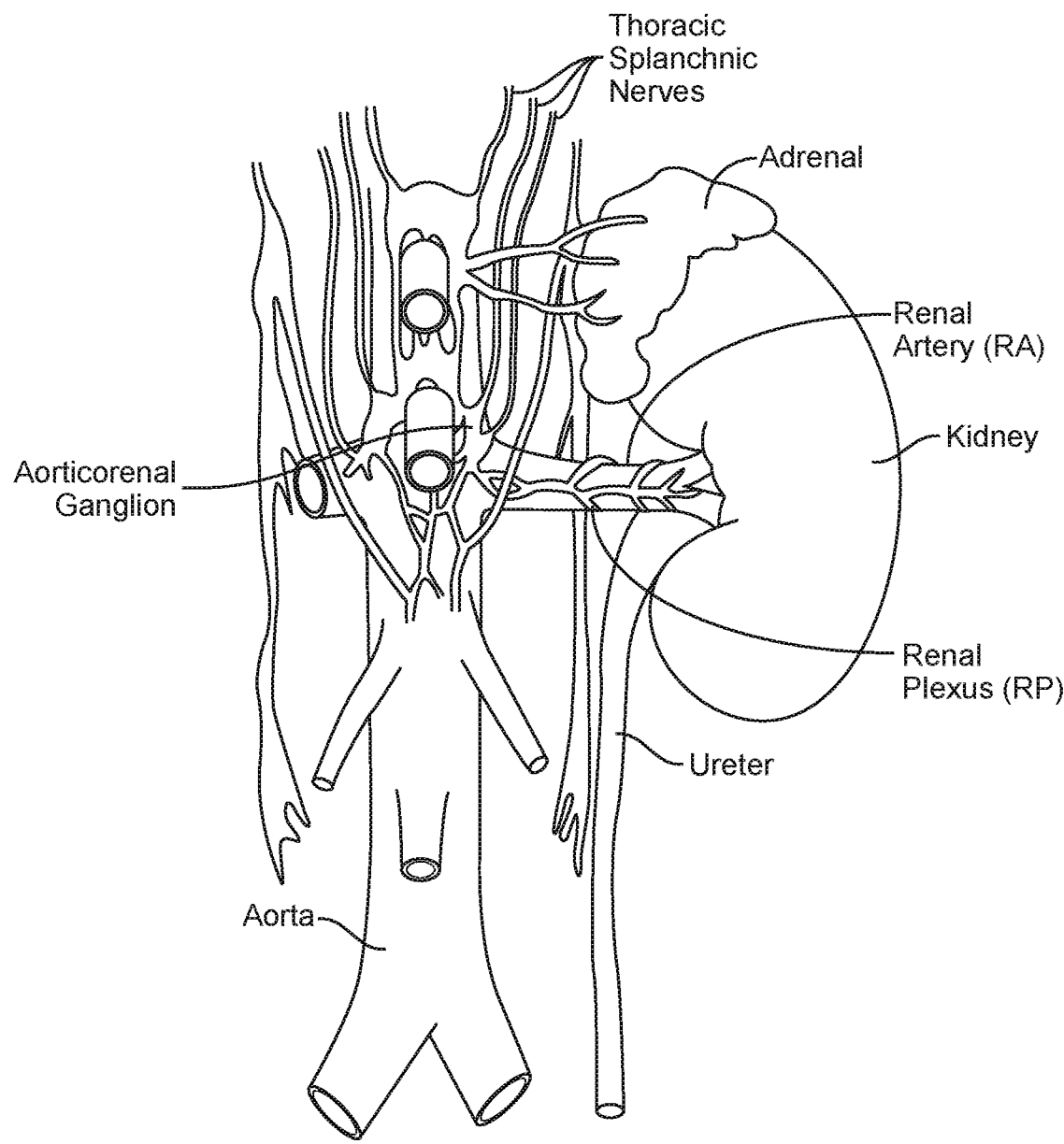
FIG. 9 is an enlarged anatomic view of nerves innervating a left kidney to form the renal plexus surrounding the left renal artery.

As FIG. 9 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

b. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

i. Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

ii. Renal Sensory Afferent Nerve Activity

Figure 10:
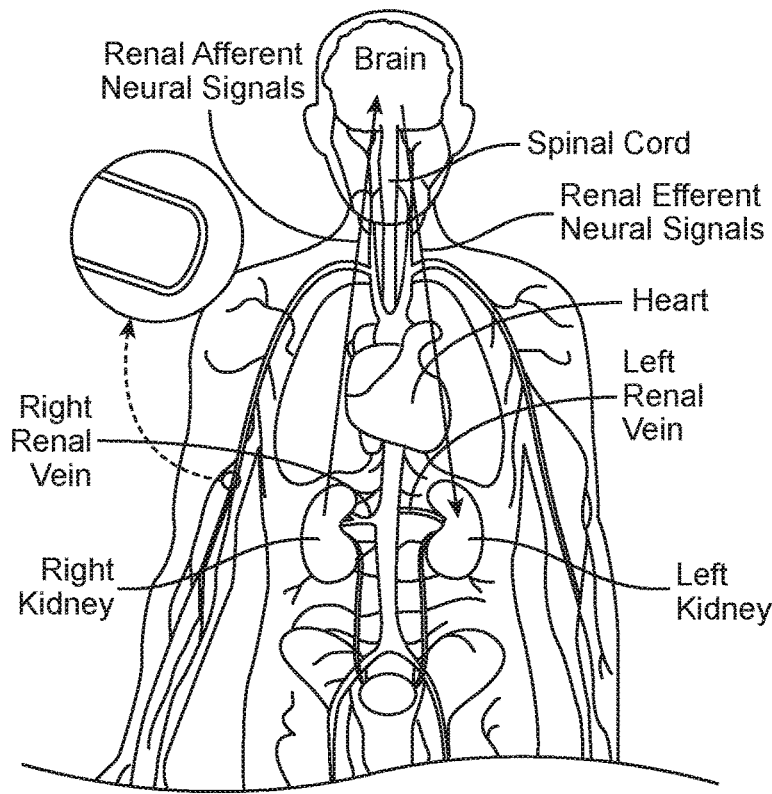
FIGS. 10 and 11 are anatomic and conceptual views, respectively, of a human body depicting neural efferent and afferent communication between the brain and kidneys.
Figure 11:
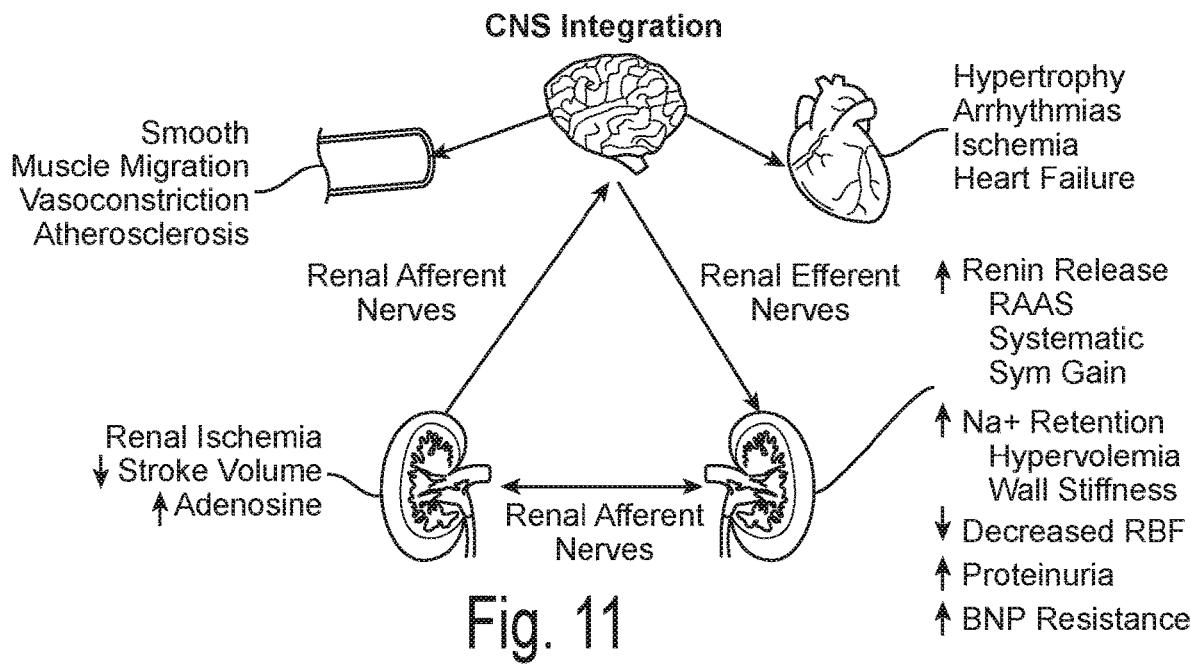

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10 and 11, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

2. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 8. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

3. Achieving Intravascular Access to the Renal Artery

Figure 12:
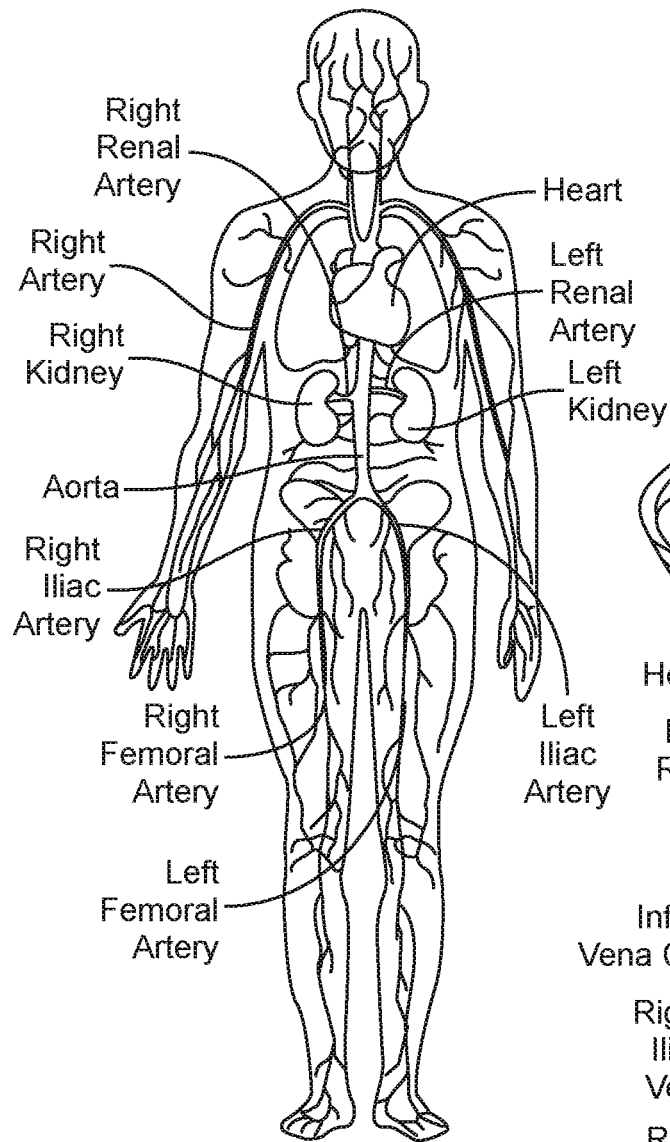
FIGS. 12 and 13 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 12 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 13:
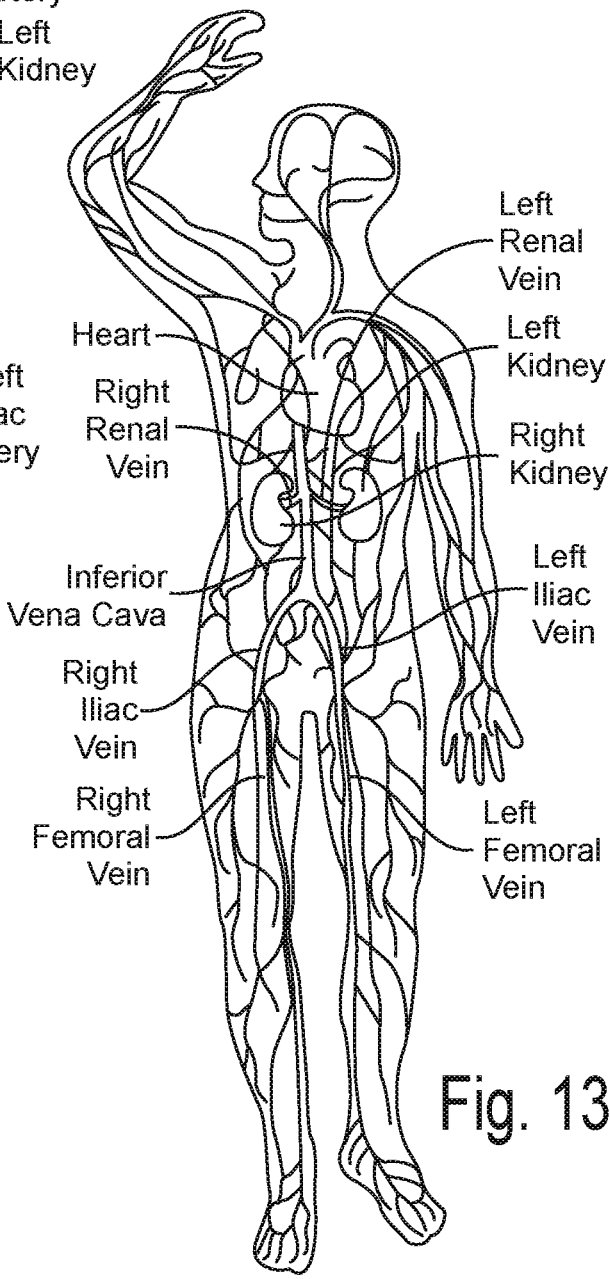

As FIG. 13 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

4. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

F. Additional Examples

Several aspects of the present technology are set forth in the following examples.

1. A neuromodulation system, comprising:
   a catheter including—
   an elongated shaft having a distal portion configured to be intravascularly positioned at a treatment site within a renal blood vessel of a human patient;
   a plurality of electrodes spaced apart along the distal portion of the shaft, wherein the electrodes are configured to deliver neuromodulation energy to target nerves at or adjacent the treatment site; and
   an irrigation outlet proximal to the electrode; and
   a controller configured to be communicatively coupled to the neuromodulation element, wherein the controller is further configured to monitor a parameter of at least one of the electrodes and tissue at or adjacent the treatment site,
   wherein the irrigation outlet is configured to direct irrigation fluid in a first direction based, at least in part, on instructions from the controller corresponding to the monitored parameter.

2. The neuromodulation system of example 1 wherein the first direction is parallel with a longitudinal axis of the renal blood vessel.

3. The neuromodulation system of examples 1 or 2, further comprising—
   an energy generator external to the patient and electrically coupled to the plurality of electrodes and the controller; and
   an irrigation pump operably coupled to the irrigation outlet and the controller,
   wherein the controller is further configured to cause the energy generator to deliver neuromodulation energy via the electrodes and cause the irrigation pump to deliver irrigation fluid via the irrigation outlet.

4. The neuromodulation system of example 3 wherein the controller is further configured to—
   compare the parameter to a predetermined parameter profile range;
   cause the energy generator to deliver neuromodulation energy at a power level in accordance with a control algorithm when the parameter is within the range;
   cause the energy generator to deliver irrigation fluid at a temperature and flow rate in accordance with the control algorithm when the parameter is within the range; and
   modify the control algorithm to adjust a characteristic of at least one of the energy and the irrigation fluid when the parameter is outside of the range.

5. The neuromodulation system of example 4 wherein the parameter is a temperature of one of the electrodes, and wherein the characteristic is a power level at which the energy is delivered, and further wherein the controller is configured to decrease the power level when the temperature of the electrodes is outside of the range.

6. The neuromodulation system of example 4 wherein the parameter is a temperature of one of the electrodes, and wherein the characteristic is a power level at which the energy is delivered, and further wherein the controller is configured to hold the power level constant or decrease the power level when the temperature of the electrode is outside of the range.

7. The neuromodulation system of examples 4 or 6 wherein the parameter is a temperature of the one of the electrodes, and wherein the characteristic is a flow rate or a temperature at which the irrigation fluid is delivered, and further wherein the controller is configured to increase the flow rate or decrease the temperature at which the irrigation fluid is delivered when the temperature of the electrode is outside of the range.

8. A system, comprising:
   a neuromodulation catheter including—
   an elongated shaft having a distal portion sized and shaped to be intravascularly positioned at a treatment site within a blood vessel of a human patient;
   an electrode configured to deliver radio frequency (RF) energy to target nerves at or adjacent the treatment site, wherein the electrode is configured to deliver the RF energy in accordance with a control algorithm; and
   a plurality of irrigation outlets positioned to release irrigation fluid in accordance with the control algorithm;
   an irrigation pump coupled to the plurality of irrigation outlets, the irrigation pump configured to deliver the irrigation fluid to the treatment site via the plurality of irrigation outlets;
   an energy generator external to the patient and coupled to the electrode and to the irrigation pump, wherein the energy generator is configured to deliver the RF energy to the target nerves via the electrode; and
   a controller communicatively coupled to the electrode, the energy generator, and the irrigation pump, wherein the controller is further configured to monitor a parameter of at least one of the electrode and tissue at or adjacent the treatment site.

9. The system of example 8 wherein a first subset of the plurality of irrigation outlets are located proximal to the electrode, and wherein the first subset of irrigation outlets are each oriented to direct irrigation fluid in a first direction.

10. The system of example 9 wherein the electrode is a first electrode, and wherein the system further comprises a second electrode on the elongated shaft spaced apart from the first electrode, and wherein the second electrode is located between the first electrode and a distal end of the elongated shaft, and further wherein the first subset is configured to release the irrigation fluid such that the irrigation fluid cools the second electrode.

11. The system of example 8 wherein the plurality of irrigation outlets are located on the elongated shaft between the electrode and a proximal portion of the elongated shaft.

12. The system of examples 10 or 11 wherein the plurality of irrigation outlets are each oriented to direct irrigation fluid radially outward from the elongated shaft.

13. The system of example 8 wherein the neuromodulation catheter further comprises an irrigation ring, and wherein the plurality of irrigation outlets are positioned on the irrigation ring.

14. The system of examples 8, 9, 10, 11, 12, or 13 wherein the parameter is a temperature of the electrode, and wherein the controller is further configured to increase a power level at which the energy generator delivers the neuromodulation energy while maintaining the temperature of the electrode within a predetermined temperature profile range.

15. The system of example 14, wherein while the controller increases the power level, the controller is further configured to (i) maintain or increase a flow rate and/or (ii) maintain or decrease a temperature at which the irrigation pump delivers the irrigation fluid.

16. The system of example 15 wherein the controller is configured to increase the power level only with an increase in the flow rate and/or only with a decrease in the temperature of the irrigation fluid.

17. The system of examples 8, 9, 10, 11, 12, 13, 14, 15, or 16 wherein the controller is configured to prevent the energy generator from increasing a power level at which the energy generator delivers the neuromodulation energy when the irrigation fluid delivered by the irrigation pump reaches a maximum flow rate and/or a minimum temperature.

18. A method, comprising:

positioning a neuromodulation catheter at a treatment site within a renal blood vessel of a human patient, wherein the neuromodulation catheter includes a treatment assembly having one or more electrodes and one or more irrigation outlets;

deploying the treatment assembly such that the one or more electrodes contact the blood vessel at the treatment site;

delivering neuromodulation energy in accordance with a control algorithm via the one or more electrodes;

monitoring a temperature of the one or more electrodes and/or a temperature of tissue of the blood vessel at or proximate to the treatment site; and delivering irrigation fluid corresponding, at least in part, to the neuromodulation energy and the monitored temperature via the one or more irrigation outlets.

19. The method of example 18 wherein delivering the neuromodulation energy in accordance with the control algorithm includes increasing a power level of the neuromodulation energy, and wherein delivering the irrigation fluid includes delivering the irrigation fluid at an increased flow rate and/or a decreased temperature corresponding to the increased power level.

20. The method of example 19, further comprising maintaining the temperature of the one or more electrodes constant and/or within an acceptable temperature range while the power level is increased.

21. The method of examples 18, 19, or 20, further comprising comparing the temperature of the one or more electrodes and/or the temperature of the tissue to a predetermined temperature profile range, and wherein delivering the neuromodulation energy in accordance with the control algorithm includes— maintaining or decreasing a power level of the neuromodulation energy when the temperature of the one or more electrodes and/or the temperature of the tissue is outside of the range; and/or increasing the power level at a slower rate when the temperature of the one or more electrodes and/or the temperature of the tissue is outside of the range.

22. The method of examples 18, 19, 20, or 21, further comprising comparing the temperature of the one or more electrodes and/or the temperature of the tissue to a predetermined temperature profile range, and wherein delivering the irrigation fluid includes delivering the irrigation fluid at an increased flow rate and/or a decreased temperature when the temperature of the one or more electrodes and/or the temperature of the tissue is outside of the range.

23. The method of examples 18, 19, 20, 21, or 22, further comprising:

comparing the temperature of the one or more electrodes and/or the temperature of the tissue to a predetermined temperature profile range;

when the temperature of the one or more electrodes and/or the temperature of the tissue is outside of the range, delivering irrigation fluid to the treatment site via the one or more irrigation outlets; and when the temperature of the one or more electrodes and/or the temperature of the tissue is inside of the range, increasing a power level at which the neuromodulation energy is delivered.

G. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Furthermore, the various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the terms "comprising," "including," "having" and "with" are used throughout to mean including at least the recited feature(s) such that any greater number of the same feature and/or additional types of other features are not precluded.

From the foregoing, it will also be appreciated that various modifications may be made without deviating from the technology. For example, various components of the technology can be further divided into subcomponents, or that various components and functions of the technology may be combined and/or integrated. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A neuromodulation system comprising:

a catheter including:

an elongated shaft having a distal portion configured to be intravascularly positioned at a treatment site within a blood vessel of a patient;

a plurality of electrodes along the distal portion of the elongated shaft, wherein the plurality of electrodes are configured to deliver neuromodulation energy at or adjacent the treatment site to form a lesion; and an irrigation outlet proximate to an electrode of the plurality of electrodes and configured to output irrigation fluid; and a controller configured to:

determine one or more of a parameter of delivery of the irrigation fluid or a parameter of delivery of the neuromodulation energy via at least one electrode of the plurality of electrodes;

determine one or more of a size or a depth of the lesion based on the one or more of the parameter of the delivery of the irrigation fluid or the parameter of the delivery of the neuromodulation energy via the at least one electrode; and adjust one or more of a characteristic of the neuromodulation energy or a characteristic of the irrigation fluid based on the determined one or more of the size or the depth of the lesion.

2. The neuromodulation system of claim 1, wherein the controller is configured to adjust the characteristic of the neuromodulation energy based on the determined one or more of the size or the depth of the lesion.

3. The neuromodulation system of claim 2, wherein the characteristic of the neuromodulation energy is a power level of the neuromodulation energy.

4. The neuromodulation system of claim 1, wherein the controller is configured to adjust the characteristic of the irrigation fluid based on the determined one or more of the size or the depth of the lesion.

5. The neuromodulation system of claim 4, wherein the characteristic of the irrigation fluid comprises one or more of temperature, flow rate, volume, or type of irrigation fluid.

6. The neuromodulation system of claim 1, wherein the controller is configured to adjust the characteristic of the neuromodulation energy and the characteristic of the irrigation fluid based on the determined one or more of the size or the depth of the lesion.

7. The neuromodulation system of claim 6, wherein the characteristic of the neuromodulation energy comprises a power level of the neuromodulation energy and the characteristic of the irrigation fluid comprises a flow rate of the irrigation fluid.

8. The neuromodulation system of claim 1, wherein the controller is configured to determine the one or more of the size or the depth of the lesion based on the parameter of the delivery of the irrigation fluid.

9. The neuromodulation system of claim 1, wherein the parameter of the delivery of the irrigation fluid includes one or more of temperature, flow rate, duration, or flow velocity.

10. The neuromodulation system of claim 1, wherein the parameter of the delivery of the neuromodulation energy includes one or more of power level, duration, impedance, or return energy.

11. The neuromodulation system of claim 1, further comprising:
an energy generator; and
an irrigation pump, wherein the controller is further configured to cause the energy generator to deliver the neuromodulation energy via the plurality of electrodes and cause the irrigation pump to deliver the irrigation fluid via the irrigation outlet.

12. A system comprising:
a neuromodulation catheter including:
an elongated shaft having a distal portion sized and shaped to be intravascularly positioned at a treatment site within a blood vessel of a patient, wherein the elongated shaft defines a plurality of irrigation outlets; and
an electrode configured to deliver energy to a target nerve at or adjacent the treatment site to form a lesion;
an irrigation pump configured to deliver irrigation fluid at or adjacent the treatment site via the plurality of irrigation outlets;

an energy generator configured to deliver the energy to the target nerve via the electrode; and
a controller configured to:
determine one or more of a parameter of delivery of the irrigation fluid or a power level of delivery of the energy via the electrode;
determine one or more of a size or a depth of the lesion based on the one or more of the parameter of the delivery of the irrigation fluid or the power level of the delivery of the energy via the electrode; and
at least one of adjust a characteristic of the energy or adjust a characteristic of the delivery of the irrigation fluid based on the determined one or more of the size or the depth of the lesion.

13. The system of claim 12, wherein the controller is configured to adjust the characteristic of the energy based on the determined one or more of the size or the depth of the lesion.

14. The system of claim 13, wherein the characteristic of the energy comprises the power level of the energy.

15. The system of claim 12, wherein the controller is configured to adjust the characteristic of the delivery of the irrigation fluid based on the determined one or more of the size or the depth of the lesion.

16. The system of claim 15, wherein the characteristic of the delivery of the irrigation fluid comprises one or more of temperature, flow rate, volume, or type of irrigation fluid.

17. The system of claim 12, wherein the controller is configured to determine the one or more of the size or the depth of the lesion based on the parameter of the delivery of the irrigation fluid.

18. The system of claim 12, wherein the controller is configured to determine the one or more of the size or the depth of the lesion based on the power level of the energy.

19. A method comprising:
delivering neuromodulation energy via at least one electrode of a plurality of electrodes of a catheter to a treatment site within a blood vessel of a patient to form a lesion;
determining, by a controller, one or more of a parameter of delivery of irrigation fluid via at least one irrigation outlet of the catheter or a parameter of delivery of the neuromodulation energy via the at least one electrode;
determining, by the controller, one or more of a size or a depth of the lesion based on the one or more of the parameter of the delivery of the irrigation fluid or the parameter of the delivery of the neuromodulation energy via the at least one electrode; and
adjusting, by the controller, one or more of one or more of a characteristic of the neuromodulation energy or a characteristic of the irrigation fluid based on the determined one or more of the size or the depth of the lesion.

20. The method of claim 19, wherein the characteristic of the irrigation fluid comprises one or more of temperature, flow rate, volume, or type of irrigation fluid, and the characteristic of the neuromodulation energy is a power level of the neuromodulation energy.

* * * * *